(12) United States Patent
Hilgers et al.

(10) Patent No.: US 8,403,663 B2
(45) Date of Patent: Mar. 26, 2013

(54) DIRECT PLACEMENT SYSTEM FOR TOOTH EXTRUSION

(75) Inventors: James J. Hilgers, Rancho Santa Fe, CA (US); Paul Gange, Itasca, IL (US)

(73) Assignee: Reliance Orthodontic Products, Inc., Itasca, IL (US)

( * ) Notice: Subject to any disclaimer, the term of this patent is extended or adjusted under 35 U.S.C. 154(b) by 0 days.

(21) Appl. No.: 13/020,537

(22) Filed: Feb. 3, 2011

(65) Prior Publication Data
US 2012/0202162 A1    Aug. 9, 2012

(51) Int. Cl.
*A61C 3/00* (2006.01)
(52) U.S. Cl. .......................................... 433/18
(58) Field of Classification Search ................ 433/1–25
See application file for complete search history.

(56) References Cited

U.S. PATENT DOCUMENTS

| | | | |
|---|---|---|---|
| 3,521,355 A * | 7/1970 | Pearlman | 433/3 |
| 3,835,538 A | 9/1974 | Northcutt | |
| 4,187,610 A * | 2/1980 | Ziegler | 433/24 |
| 4,472,137 A * | 9/1984 | Barone | 433/3 |
| 4,861,268 A * | 8/1989 | Garay et al. | 433/229 |
| 4,869,667 A * | 9/1989 | Vardimon | 433/24 |
| 4,889,485 A | 12/1989 | Iida | |
| 5,018,259 A * | 5/1991 | Wildman | 29/896.11 |
| 5,040,981 A * | 8/1991 | Oliva | 433/141 |
| 5,064,369 A * | 11/1991 | Kawaguchi | 433/3 |
| 5,078,597 A * | 1/1992 | Caplin | 433/18 |
| 5,110,290 A * | 5/1992 | Wong | 433/9 |
| 5,112,221 A * | 5/1992 | Terry | 433/21 |
| 5,176,517 A * | 1/1993 | Truax | 433/180 |
| 5,242,302 A * | 9/1993 | Riehm | 433/164 |
| 5,292,249 A * | 3/1994 | German | 433/22 |
| 5,681,163 A * | 10/1997 | Wolk | 433/3 |
| 5,759,028 A * | 6/1998 | Bozman | 433/9 |
| 5,820,368 A * | 10/1998 | Wolk | 433/3 |
| 6,354,833 B1 * | 3/2002 | Townsend-Hansen | 433/8 |
| 6,746,241 B2 * | 6/2004 | Townsend-Hansen | 433/8 |
| 7,097,449 B2 * | 8/2006 | Jessop et al. | 433/8 |
| 7,335,021 B2 * | 2/2008 | Nikodem | 433/18 |
| D602,160 S * | 10/2009 | Yazdi | D24/156 |
| 2003/0049583 A1 * | 3/2003 | Pitnick et al. | 433/18 |
| 2003/0068595 A1 * | 4/2003 | Pitnick et al. | 433/18 |
| 2004/0166461 A1 * | 8/2004 | Devincenzo | 433/18 |
| 2005/0064359 A1 * | 3/2005 | Nikodem | 433/18 |
| 2007/0264607 A1 * | 11/2007 | Olavarria Landa | 433/18 |
| 2008/0182219 A1 * | 7/2008 | Spalty | 433/22 |
| 2008/0254401 A1 * | 10/2008 | Yazdi | 433/18 |

* cited by examiner

*Primary Examiner* — Cris L Rodriguez
*Assistant Examiner* — Matthew Saunders
(74) *Attorney, Agent, or Firm* — Ice Miller LLP (57) ABSTRACT

An orthodontic apparatus for direct placement of a ligature for tooth extruding. The apparatus has a body having a first end and a second end. The first end has a reservoir for receiving adhesive and a ligature having a first end and a second end. The first end is releasably embedded in the reservoir and the second end extends through the body.

21 Claims, 6 Drawing Sheets

DIRECT PLACEMENT SYSTEM FOR TOOTH EXTRUSION

BACKGROUND OF THE INVENTION

This invention relates to impacted teeth and, specifically, to a method and apparatus to facilitate placement of a system to aid in extrusion and positioning of such teeth. In general, the present invention is less invasive than previous products and methods of extruding impacted teeth, thus, making the extrusion of the tooth more comfortable for the patient. Another object of the invention is that it provides an easier, more comfortable removal of the apparatus used to extrude the impacted tooth from the surface of the tooth.

Treatment of an unerupted tooth generally involves both oral surgery to expose a significant portion of the impacted tooth and use of orthodontics to apply tension or traction to cause the tooth to erupt and bring the tooth into its proper position. Typically the orthodontics used to facilitate the extrusion of the tooth must be forcibly fractured off the surface of the tooth after it has been moved into the desired position. Such a removal process can be uncomfortable or even painful for the patient. Various products and methods have been developed to address this problem with varying levels of success.

One such apparatus and method of treatment is disclosed in U.S. Pat. No. 4,187,610, Ziegler, Feb. 12, 1980. Ziegler discloses use of a ligation chain that has a large loop at one end followed by a series of smaller loops. The large loop encircles and is tightened around the surgically exposed anatomic crown of the impacted tooth. The smaller loops are connected to an elastic ligature thread that is then attached to an arch wire, bracket, or similar conventional orthodontic apparatus to apply tension to the impacted tooth. One disadvantage of such an approach is that the oral surgeon must expose a significant amount of the impacted tooth to enable the ligation chain to be looped around the tooth below the crown, resulting in a rather invasive procedure for the patient. The wire looped around the tooth can also slip out of position during traction, possibly necessitating additional surgery. Additionally, the removal of the device involves cutting and pulling of the wire, causing patient discomfort.

Yet another approach involves bonding some type of fastener to the surface of the impacted tooth. Such an approach is disclosed in U.S. Pat. No. 3,835,538, Northcutt, Sep. 17, 1974; U.S. Pat. No. 7,335,021, Nikodem, Feb. 26, 2008; and U.S. Pat. No. 6,354,833, Townsend-Hansen, Mar. 12, 2002.

Northcutt discloses bonding a curved onlay to the surface of the impacted tooth that has a means to attach a ligature, such as a plastic loop, integrated in the onlay. However, Northcutt admits in col. 2, l. 49-52 that the onlays will not fit the teeth of one-tenth of people, requiring correction of the shape of the onlay using a dental burr by the orthodontist or surgeon. Northcutt still requires exposure of about one-third of the cuspid crown for placement of the onlay (col. 1, l. 46-47). Also, after the tooth has been erupted and moved into the desired position, the onlay must be forcibly removed or fractured from the surface of the tooth.

Nikodem similarly discloses use of an orthodontic fixture bonded to the surface of the impacted tooth as a means to attach a ligature. Such a fixture can include an orthodontic bracket. An example of an orthodontic bracket specifically used in extrusion of impacted teeth is disclosed in Townsend-Hansen. However, conventional brackets can cause irritation and can be difficult to precisely position and bond to the surface of an impacted tooth. Additionally, an intermediary mesh backing is typically associated with brackets to either carry adhesive or provide a bonding site. Failure of the bond can and often does occur at the contact point between the mesh and the surface of the tooth or the contact point between the mesh and the bracket or other orthodontic fixture. Fixtures or brackets such as those disclosed in Nikodem and Townsend-Hansen must be forcibly fractured off the surface of the tooth, causing significant patient discomfort.

U.S. Pat. No. 5,112,221, Terry, May 12, 1992 discloses an extrusion spring arm for facilitating the eruption of an impacted tooth. The arm has an eyelet that is bonded to the impacted tooth. However, the patent does not disclose specifically how the eyelet is bonded to the tooth, only that it is bonded on the tooth.

U.S. Pat. No. 5,829,368, Wolk, Oct. 13, 1998 and U.S. Pat. No. 5,681,163, Wolk, Oct. 28, 1997 disclose-disposable applicators for bonding and retaining orthodontic attachments, such as wires, to the front or back surface of fully erupted teeth. The orthodontic attachments are described as wires or conventional brackets or rubber bands to correct the irregular teeth of the patient.

The present invention addresses these problems by requiring only minimal access to the surface of the impacted tooth, enabling adhesive to conform to any tooth's surface and being easily removable after eruption and positioning of the tooth.

SUMMARY OF THE INVENTION

The invention comprises a method and apparatus for positioning and bonding a ligature directly to the surface of an impacted tooth for use in extruding said tooth. By use of this invention an intermediary mesh base, which can fail in a moist environment because of its dependency on access and approximation of the mesh-based bracket to tooth interface, is no longer required, thus, providing a more secure attachment of the ligature to the impacted tooth. Additionally, fracturing off the intermediary mesh-based bracket is no longer required. Instead, a dental adhesive material, preferably a light-curable dental composite, is used to bond the ligature to the surface of the tooth. Such composites can be gently polished off of the tooth after extrusion is completed, greatly increasing patient comfort. The dental adhesive materials are selected from flowable materials, permitting them to conform precisely to the surface of the tooth, avoiding the necessity of individually shaping preformed onlays and facilitating the integrity of the ligature-tooth bond.

DETAILED DESCRIPTION OF THE INVENTION

Figure 1:
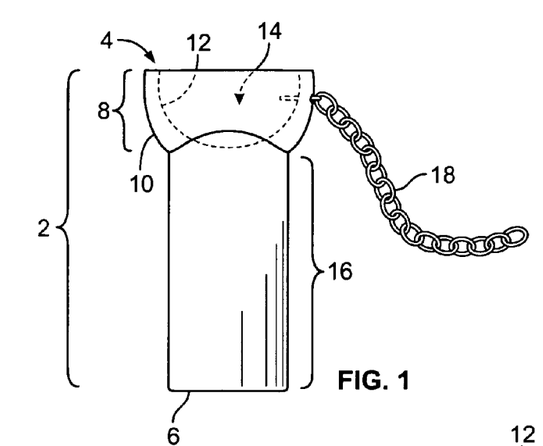
FIG. 1 is a side view of an embodiment of the invention.
Figure 2:
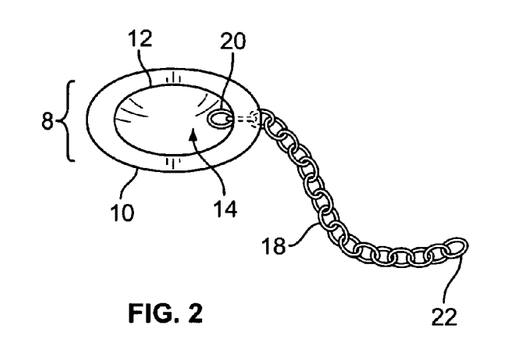
FIG. 2 is a top view of an embodiment of the invention.
Figure 3:
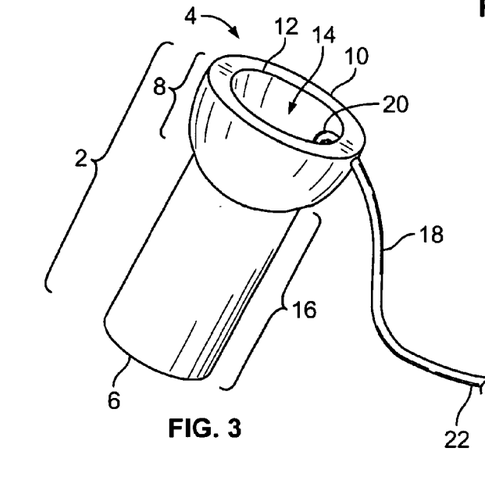
FIG. 3 is a perspective view of an embodiment of the invention.

As shown in FIGS. 1-3, the present invention comprises a body 2 having a first end 4 and an opposite second end 6 where the first end comprises a cup portion 8 having an outer surface 10 and an inner surface 12, the inner surface forming a reservoir 14 for receiving a dental adhesive material. The second end comprises preferably a shaft portion 16 that functions as an aligner of the first end on the surface of the target tooth to be extruded. A ligature means 18 has a first end 20 associated with the cup and reservoir portions of the body and a second end 22. FIGS. 1-3 show a presently preferred embodiment where the first end 20 of the ligature 18 is releasably embedded in the reservoir 14 of the body 2 and the second end 22 extends through and outwardly from the side of the cup portion of the body. In an alternative embodiment, the ligature 18 is releasably embedded in the reservoir 14 of the body 2 by the orthodontist or oral surgeon prior to use, preferably by making a thin slit in the side wall of the cup portion 8 and sliding the first end of the ligature into the slit so that a small portion of the ligature extends into the reservoir, such as one to two links length of a conventional gold ligature chain. In a preferred embodiment, the body 2 is made of translucent silicone and measures approximately 8 mm tall, cup portion 8 is oval shaped and measures approximately 5 mm long and 3 mm wide and reservoir 14 has a depth of approximately 2 mm. The body 2 can be made of any suitable material that allows releasable embedding of the ligature. Preferably the cup portion of the body is slightly elastic to permit easy slitting by the dental professional and partial deformation when it is brought into contact with the tooth surface to facilitate full and complete contact of the dental adhesive material with the tooth surface, whatever its conformation. However, it should be understood that the body 2 can be of any size and shape appropriate for applying an adhesive dental material with an embedded ligature to the surface of an impacted tooth.

In a preferred embodiment, the ligature 18 is a gold chain that is approximately 1.91 cm (0.75 in) long where only the first link or two of the first end 20 of the chain is releasably embedded in the reservoir and the second end extends through the body approximately 2 mm from the top rim of the reservoir. Such embedding may be accomplished by making a small hole in the side of the reservoir below its rim, the hole having a diameter similar to that of the ligature means. However, it should be understood that the ligature 18 can consist of any orthodontic grade material appropriate for use in extruding an impacted tooth and that can be embedded in the reservoir, such as a wire, as shown in FIG. 3.

The adhesive dental material, in the preferred embodiment, is a light-cured composite, such as Flow Tain™ sold by Reliance Orthodontics, Inc., Itasca, Ill. However, any appropriate orthodontic grade adhesive material capable of bonding to tooth enamel while providing sufficient strength for subsequent extruding force to be applied can be used, including material that also contains self-curing components. Also contemplated is the addition of other beneficial compositions to the adhesive material, such as fluoride release and anti-bacterial compositions.

Figure 4:
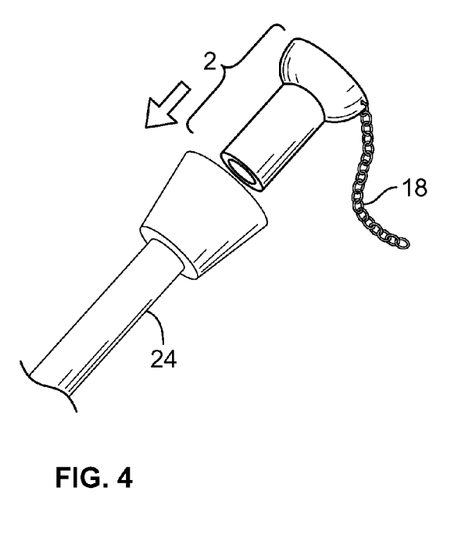
FIG. 4 is a view of an embodiment of the invention including an optional wand.
Figure 5:
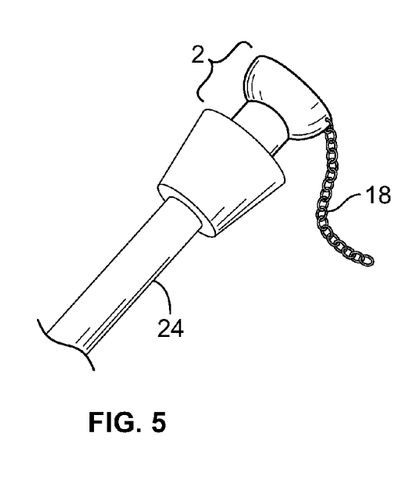
FIG. 5 is a view of an embodiment of the invention wherein the body and ligature have been placed in the wand shown in FIG. 4.

In an embodiment shown in FIGS. 4-5, a wand 24 can be used to more efficiently and precisely position the body 2 against the exposed surface of an impacted tooth. In a preferred embodiment, wand 24 engages the shaft portion 16 and is angled at one end to facilitate placement of the ligature and the dental adhesive material on the surface of the impacted tooth at its desired location.

FIGS. 4-13 depict a present method of using an embodiment of the invention and will be described in more detail below.

As shown in FIGS. 4 and 5, the shaft portion 16 of the body 2 is inserted into a wand 24 to facilitate handling and positioning of the body during filling of the cup portion 8 with dental material and subsequent placement of the dental adhesive material on the target extruded tooth. FIG. 4 depicts an embodiment in which the ligature is already releasably embedded in the reservoir 14 of the body 4.

Figure 6:
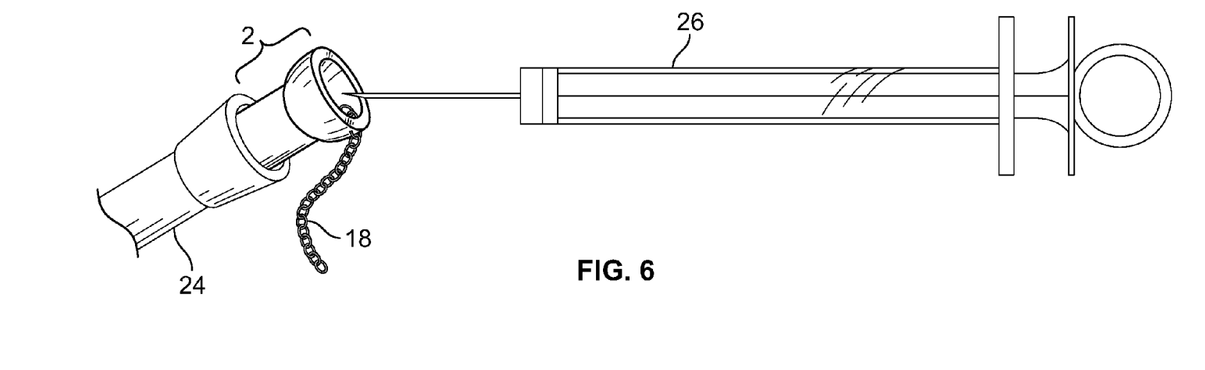
FIG. 6 is a view of an embodiment of the invention showing the reservoir being filled with a dental adhesive material using a syringe.
Figure 7:
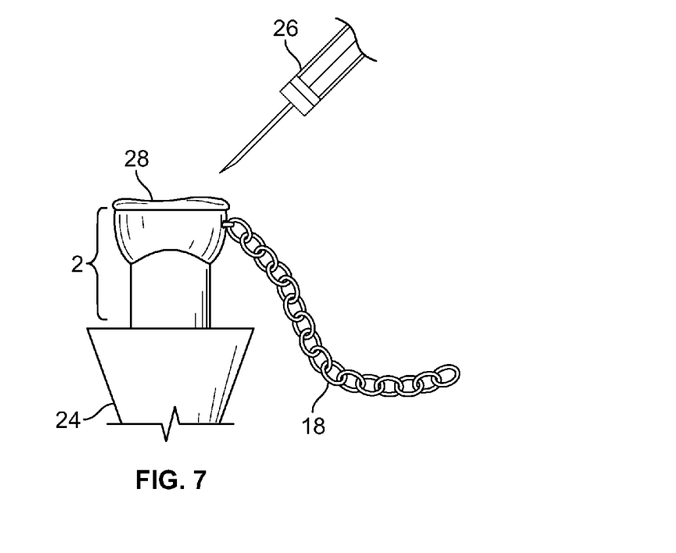
FIG. 7 is a view of an embodiment of the invention filled with the adhesive material.

Next, as illustrated in FIG. 6, a needle-tip dispenser 26, such as a composite needle-type syringe, is used to fill the reservoir 14 with a dental adhesive material. One such needle-tip dispenser is included with the light-curable Flow Tain™ composite kit mentioned above. The body 2 is filled with adhesive material 28 so that the meniscus of the adhesive is visible just above the first end 4 of the body 2, as shown in FIG. 7.

Figure 8:
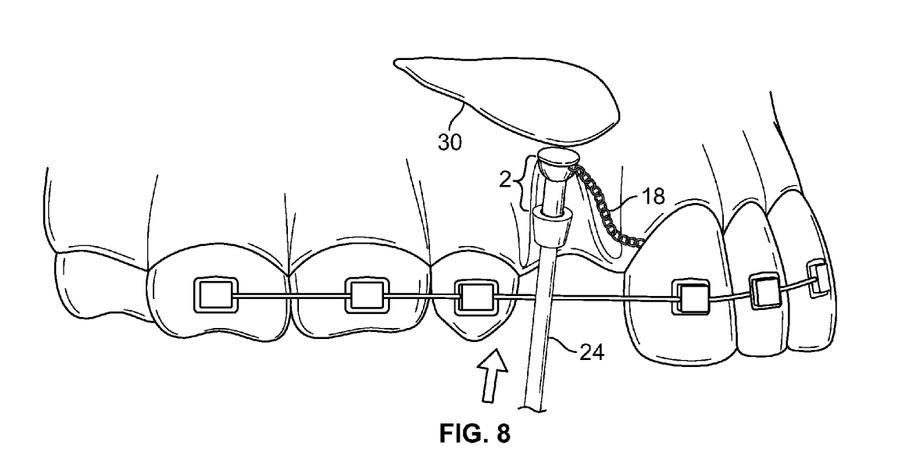
FIG. 8 is a view of an embodiment of the invention being positioned on the surface of an impacted tooth.
Figure 9:
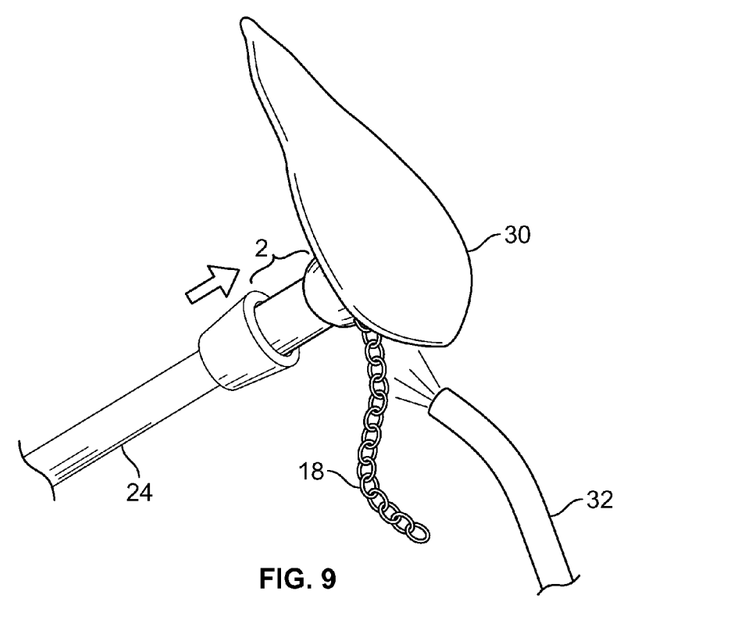
FIG. 9 is a view of an embodiment of the invention showing the adhesive material being light cured while in contact with the tooth surface.

The oral surgeon uses the wand 24 to position the adhesive filled body 2 on the surface of an impacted tooth 30 that has been surgically exposed, illustrated in FIG. 8. As further shown in FIG. 8, the dental practitioner need expose only a portion of the tooth surface, and does not need to cut below the level of the tooth crown to effect placement. In an embodiment illustrated in FIG. 9, the adhesive material is light cured while being held in contact with the exposed tooth surface using light curing device 32.

Figure 10:
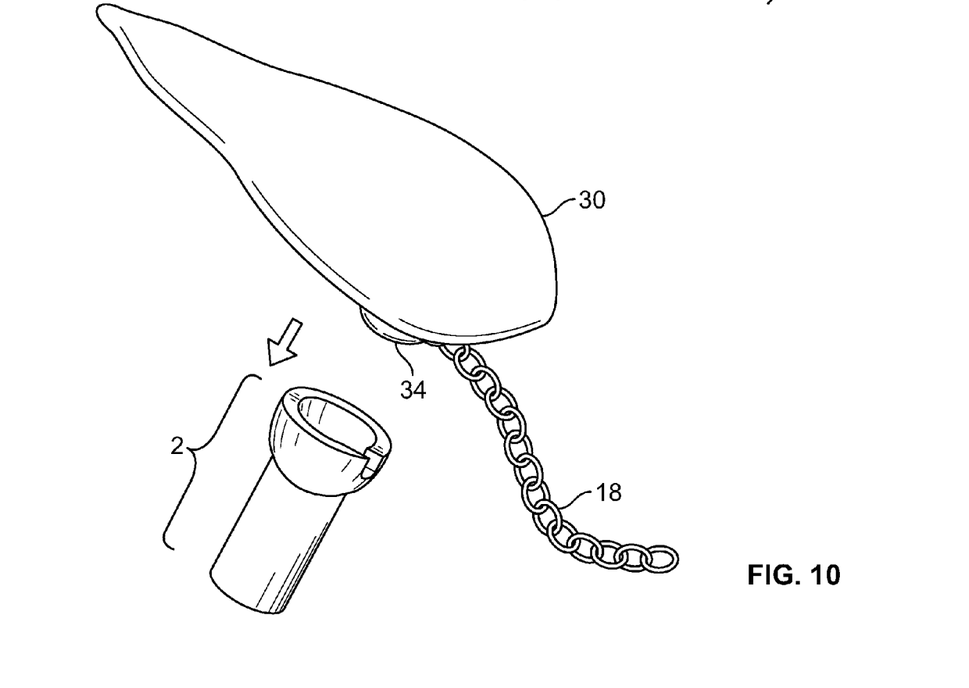
FIG. 10 is a view of an embodiment of the invention showing the body being removed from the surface of an impacted tooth having a partially exposed tooth surface.
Figure 11:
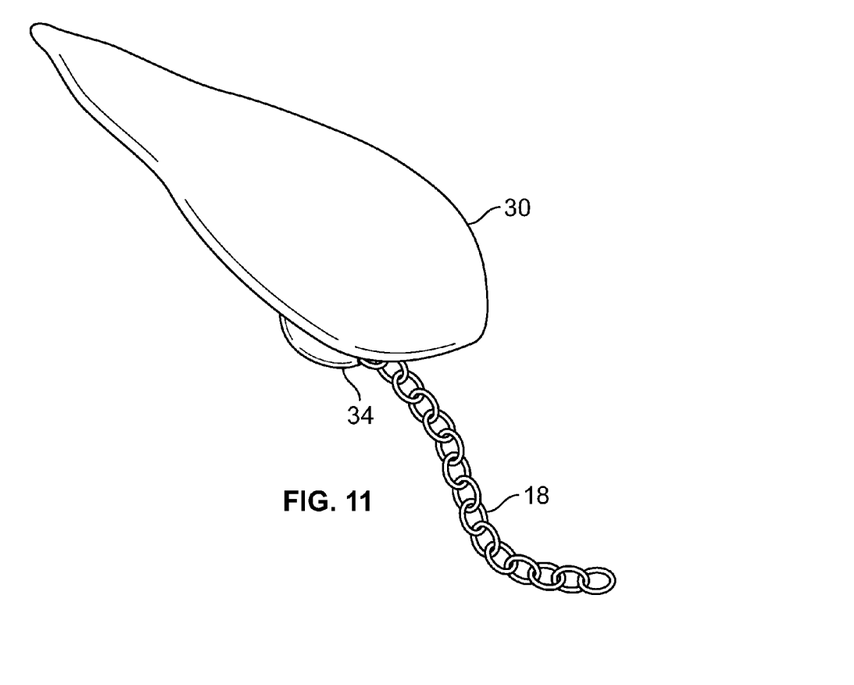
FIG. 11 is a view of an embodiment of the invention showing the cured adhesive material containing the ligature bonded to the surface of an impacted tooth.

After the adhesive is sufficiently cured, typically by 10-30 seconds of exposure from light curing device 32, body 2 is removed, as shown in FIG. 10, leaving ligature means 18 bonded to the exposed surface of impacted tooth 30. As illustrated in FIG. 11, a small button of cured adhesive material 34 including the ligature remains on the surface of the tooth.

Figure 12:
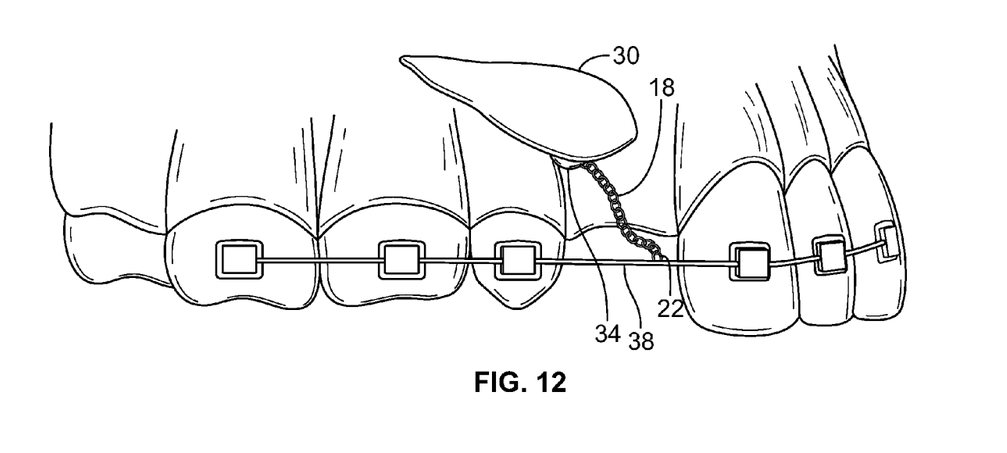
FIG. 12 is a view of an embodiment of the invention showing the cured adhesive material and ligature from FIG. 11 coupled to an apparatus attached to an upper row of teeth from which tension may be applied to the impacted tooth through the ligature.
Figure 13:
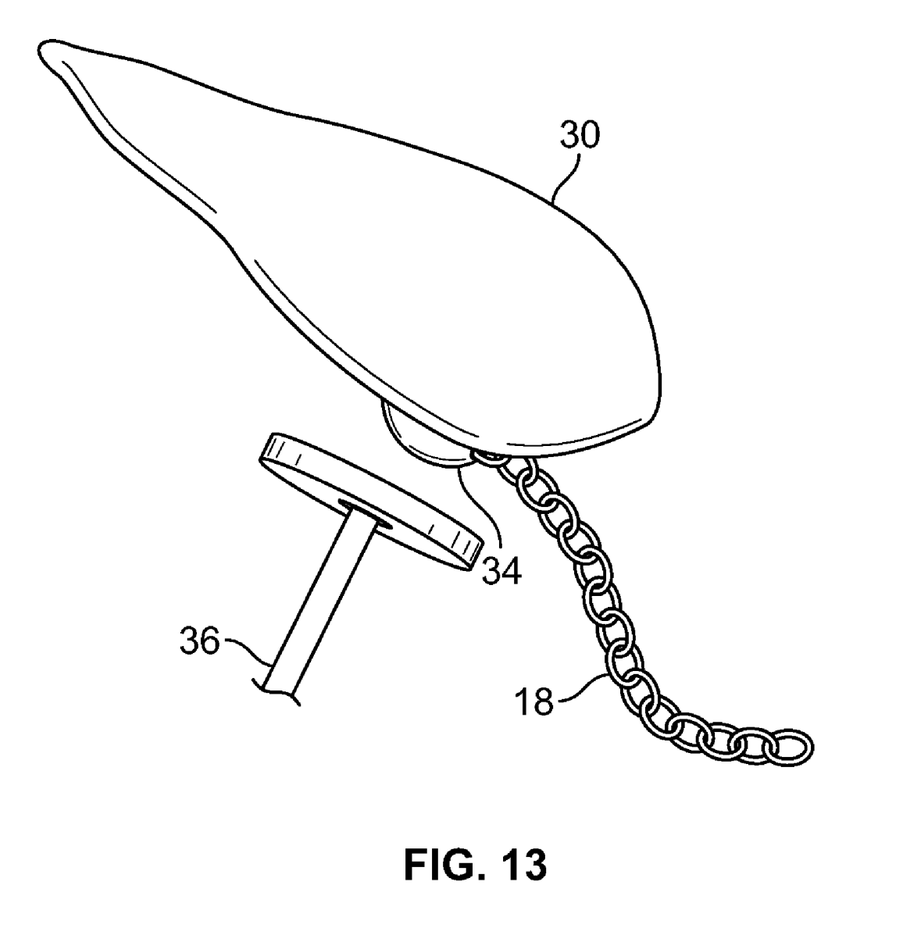
FIG. 13 is a view of an embodiment of the invention showing removal of the cured adhesive material and ligature after extrusion is complete by polishing away the dental material using a conventional dental polishing wheel.

The second end 22 of the ligature is attached to any well-known system, such as an arch wire 38, as shown in FIG. 12, bracket or the like to provide a base from which appropriate tension may be applied from the base to the tooth through the ligature to erupt the impacted tooth into the desired location. Conventional elastic thread, springs or other ligation force applying means well-known in the art may be employed, and forces of around 1 and ½ to 2 ounces gravitational force may be used to effect extruding and placement. Other forces could also be employed depending on the specific physiology of the patient. As shown in FIG. 13, once the tooth has erupted and is in the desired location, ligature 18 is easily removed by polishing off the cured dental material from the tooth surface by well-known techniques, such as by use of polishing wheel 36 and/or dental burs.

An aligner attachment kit of the present invention is contemplated that can include a combination of the body described above with a ligature, and, optionally, a wand, a needle-tip dispenser, and/or a dental adhesive material. The ligature can be provided separately or pre-embedded in the body. If provided separately, a selection of various types of ligatures can be included, such as chains and wires of different materials and thicknesses.

EXAMPLE

Materials

A prototype of a preferred embodiment of the invention was created and tested in several patients. The body was made of silicone, about 8 mm in length, and the reservoir was an oval shaped cup located at one end with dimensions of about 5 mm long by 3 mm wide by 2 mm deep in terms of its reservoir. The ligature was a small diameter gold chain about 2 cm in total length that was releasably mounted in the reservoir by being embedded about 2 mm below the surface of the cup portion and extending about 1 mm into the reservoir. Also included was a wand having an angled head that held the body to allow for accurate placement. The adhesive provided with the prototype was Flow Tain™ flowable light cure adhesive available from Reliance Orthodontic Products, Inc. Flow Tain™ has a low modulus of elasticity and is highly polishable. The thixotropic properties of Flow Tain™ prevent the composite from slumping and allows for better control of the material. The Flow Tain™ composite came with its own needle tip dispenser for use in dispensing the composite into the reservoir of the body.

Procedure

The technique used to test the prototype involved the following: 1) surgically exposing a portion of the impacted tooth surface, here the front surface of a cuspid tooth; 2) drying the exposed tooth surface; 3) etching and preparing the etched enamel of the exposed tooth surface by using a conventional etchant/dental bonding resin; 4) placing the prototype in a wand; 5) filling the reservoir of the prototype with Flow Tain™ flowable composite so that the chain end embedded in the reservoir is completely surrounded by the composite; 6) gently placing, without applying significant pressure, the composite filled prototype on the surface of the exposed tooth using the wand, making sure the composite is in flush contact with the tooth; 7) light curing the composite, preferably for about 20 seconds in accordance with the manufacturer's recommended procedures of use for the Flow Tain™ composite; 8) removing the cup portion by simple pulling, which easily broke the cup portion away from the chain leaving a button of cured composite material with the chain embedded on the surface of the tooth; and 9) closing the exposed site as necessary and attaching the gold chain using a conventional tie down method determined at the orthodontist's discretion, which typically involves using a thin wire or an elastic thread to tie the chain to an arch wire or bracket.

Results

An oral surgeon applied the prototype in accordance with the aforementioned procedure to patient A's impacted cuspid. After 5 months, the extruding process proceeded normally, with the chain attached to an archwire by an elastic thread that applied about 1.5 to 2.0 ounces of pressure to the impacted tooth.

What is claimed is:

1. An orthodontic apparatus for direct placement of a ligature for tooth extruding, comprising:
    a body having a first end and a second end, wherein the first end comprises a cup portion having an outer surface and an inner surface, the inner surface forming a reservoir for receiving a dental adhesive material capable of bonding to a surface of the tooth being extruded, and the second end comprises a shaft portion for alignment of the first portion on the tooth surface; and
    a ligature means having a first end and a second end wherein the first end has a portion releasably embedded in the reservoir and the second end extends outwardly from the body and is capable of engaging a tooth extruding pulling force means.

2. The orthodontic apparatus of claim 1 wherein the first end of the body is silicone.

3. The orthodontic apparatus of claim 1 wherein the ligature means is a chain.

4. The orthodontic apparatus of claim 1 wherein the ligature means is a wire.

5. The orthodontic apparatus of claim 3 wherein the chain is made of gold.

6. The orthodontic apparatus of claim 1 wherein the cup portion is oval shaped.

7. The orthodontic apparatus of claim 1 wherein said first end portion of the ligature means extends through the side of the cup portion.

8. The apparatus of claim 1 wherein the second end of the ligature means extends outwardly through the body at approximately 2 mm from the first end of the body.

9. The apparatus of claim 1 further comprising a wand capable of receiving the shaft portion of the body for positioning of the cup portion of the body on the surface of the tooth.

10. The apparatus of claim 1 wherein the dental adhesive material is a light curable composite material.

11. A method for aiding the eruption of an impacted tooth, comprising:
    providing a body having a first end and a second end wherein the first end comprises a cup portion having an outer surface and an inner surface, the inner surface forming a reservoir for receiving a dental adhesive material capable of bonding to the surface of the tooth being extruded, and the second end comprises a shaft portion for alignment of the first portion on the tooth surface;
    providing a ligature having a first end and a second end wherein a portion of the first end is releasably embedded in the reservoir and another portion of the first end extends into the reservoir and the second end extends outwardly from the body;
    exposing a portion of the surface of the tooth to be extruded;
    filling the reservoir of the body with a dental adhesive material;
    positioning the reservoir and the dental adhesive material on the exposed surface of the tooth;
    curing the adhesive material within the reservoir while in contact with the tooth surface; and
    removing the reservoir and the body, leaving the first end of the ligature bonded to the surface of the tooth.

12. The method of claim 11 wherein the exposed surface of the tooth is dried before placement of the adhesive material.

13. The method of claim 11 wherein the exposed surface of the tooth is acid etched before placement of the adhesive material.

14. The method of claim 11 wherein the exposed surface of the tooth is sealed before placement and curing of the adhesive material.

15. The method of claim 11 wherein the body is positioned on the surface of the tooth using a wand having a portion capable of receiving the shaft portion of the body.

16. The method of claim 11 wherein the adhesive material is a light curable dental composite material.

17. The method of claim 16 wherein the adhesive material is light cured after the body is positioned on the surface of the tooth.

18. The method of claim 16 wherein the adhesive material comprises a self-cure composition and a light cure composition.

19. A kit for aiding the eruption of an impacted tooth, comprising:

an adhesive application and ligature positioning means comprising a body having a first end and a second end wherein the first end comprises a cup portion having an outer surface and an inner surface, the inner surface forming a reservoir for receiving a flowable adhesive material capable of bonding to the surface of the tooth being extruded upon curing of the material and for receiving a ligature means disposed within the reservoir, and the second end comprises a shaft portion for alignment of the first end on the tooth surface; and a ligature means having a first end and a second end wherein the first end is releasably embedded in the reservoir of the application means and extends into the reservoir so as to be brought into contact with the adhesive material when the reservoir is filled with the material and the second end of the ligature means ends outwardly from the body.

20. A kit according to claim 19 wherein the kit further comprises a wand means for releasably holding the shaft portion of the application means during alignment of the cup portion of the application means on the tooth surface.

21. A kit according to claim 19 wherein the kit further comprises a dental adhesive material capable of bonding to the tooth surface upon curing and retaining the first end of the ligature means in place on the tooth surface.

* * * * *